United States Patent [19]

Sturwold et al.

[11] 3,970,569
[45] July 20, 1976

[54] WATER SOLUBLE TRIGLYCERIDE COMPOSITIONS AND METHOD FOR THEIR PREPARATION

[75] Inventors: Robert J. Sturwold; Fred O. Barrett, both of Cincinnati, Ohio

[73] Assignee: Emery Industries, Inc., Cincinnati, Ohio

[22] Filed: Aug. 28, 1975

[21] Appl. No.: 608,764

Related U.S. Application Data

[62] Division of Ser. No. 438,283, Jan. 31, 1974, Pat. No. 3,928,401.

[52] U.S. Cl. ............................................. 252/49.3
[51] Int. Cl.² ......................................... C10M 1/06
[58] Field of Search ............ 252/49.3, 56 S, 56 TD, 252/49.5

[56] References Cited
UNITED STATES PATENTS

| | | | |
|---|---|---|---|
| 3,492,232 | 1/1970 | Rosenberg | 252/49.5 X |
| 3,634,245 | 1/1972 | Meisters | 252/49.5 X |
| 3,657,126 | 4/1972 | Sawyer | 252/49.5 |
| 3,915,872 | 10/1975 | Sturwold et al. | 252/56 S X |

Primary Examiner—Delbert E. Gantz
Assistant Examiner—Andrew H. Metz
Attorney, Agent, or Firm—Gerald A. Baracka; John D. Rice

[57] ABSTRACT

Water soluble mixed ester lubricants derived from triglycerides are obtained by transesterifying a triglyceride with a low molecular weight polyoxyethylene glycol in the presence of short-chain mono- or dicarboxylic acids. The mixed ester compositions of this invention are readily water soluble and are excellent lubricants for metalworking operations. Water solubility is achieved with the present mixed ester products even though they have higher triglyceride contents than previously known ester lubricants.

4 Claims, No Drawings

WATER SOLUBLE TRIGLYCERIDE COMPOSITIONS AND METHOD FOR THEIR PREPARATION

This is a division of application Ser. No. 438,283, filed Jan. 31, 1974 now U.S. Pat. No. 3,928,401.

BACKGROUND OF THE INVENTION

The reaction of triglycerides and polyoxyethylene glycols to obtain mixed esters is known. For example, British Pat. No. 847,517 shows the reaction of 2 mols trilyceride with 1 mol polyoxyethylene glycol at an elevated temperature in the presence of a catalyst to obtain partial interesterification while avoiding complete deesterification of the triglyceride. The resulting mixed ester compositions, consisting of mono-, di- and triglycerides with mono- and diesters of polyoxyethylene glycol, are miscible with hydrocarbons and emulsifiable with water. The ready emulsifiability of these materials is the result of a substantial portion of the mixture being mono- and diesters of polyoxyethylene glycols which are known nonionic surface active agents. U.S. Pat. No. 3,202,607 shows the formation of polyoxyethylene adducts of castor oil containing from about 10% to about 80% by weight combined ethylene oxide and the combination of the resulting adducts with propylene glycol or dipropylene glycol to provide functional fluids for use as aqueous dispersions in the working of alloys and steels.

While emulsions and dispersions of lubricant esters are acceptable in many applications there are some common problems associated with their use for lubrication. Their biggest drawback is the tendency to separate upon standing. Even the best lubricant ester emulsions are not stable indefinitely and upon prolonged standing, such as during storage, the emulsions separate and thus require re-emulsification which is costly and time-consuming. Additionally, it is often difficult to obtain uniform lubrication with lubricant emulsion systems particularly in high-speed operations. For these and other reasons the trend has been toward the use of lubricants which are water soluble, as opposed to those which are only emulsifiable or dispersible in water (see U.S. Pat. No. 3,676,345). Clear lubricant solutions are especially desirable since they have the added advantage that the operators can constantly visually monitor the lubricant and determine the amount of contaminants, such as dirt and scale, picked up during the operation.

U.S. Pat. No. 3,634,245 discloses ester lubricants which are soluble in 100°F water but which have distinct cloud points below 180°F and a two-step process for their preparation. To obtain the "water soluble" products of the invention castor oil is first transesterified with about 0.75 to about 2.0 mol equivalents polyoxyethylene glycol having a molecular weight of at least 1000 until the reaction product is soluble, i.e., when 5 grams of the product are completely soluble in 100 mls of water at 100°F. The product is then further modified in a separate and distinct step by reacting with a mono- or dicarboxylic acid. The second reaction is continued until the acid number of the composition falls below about 6. This product is then diluted with water to obtain aqueous solutions containing about 5 to about 50% by weight of the ester product.

While the ester compositions of the U.S. Pat. No. 3,634,245 are useful lubricants they are not completely soluble in water at room temperature and they have distinct cloud points below 180°F. Other disadvantages are that the process requires two distinct reaction steps and is apparently limited to use with castor oil if useful products are to be obtained. Additionally, in order to obtain useful ester compositions polymeric alkylene oxide glycols having molecular weights of at least 1000 are necessarily employed.

It would be extremely useful and advantageous if water soluble triglycerides could be obtained employing a one-step process and if the resulting products were readily soluble in cold water to give clear aqueous solutions. It should be still more useful if a wide variety of triglycerides and low molecular weight polyoxyethylene glycols could be used to obtain useful lubricants. The advantages of this latter feature will become more evident as the instant invention is described more fully.

SUMMARY OF THE INVENTION

We have now discovered mixed ester products obtained by a single-step transesterification reaction of triglycerides, low molecular weight (less than 1000) polyoxyethylene glycols and short-chain mono- or dibasic acids which are readily soluble in cold water in all proportions to provide clear lubricant solutions. Aqueous solutions of these esters have superior lubricating properties. Additionally, the present lubricants have negative heats of solution so that while they are completely soluble in water at lower temperatures they come out of solution as the temperature is raised. This feature is highly desirable in certain metalworking operations, such as hot rolling, since the ester lubricant will deposit from solution onto the surface of the metal to provide more effective lubrication.

Over and above the desirability of having water soluble ester lubricants with improved properties and negative heats of solution, the utility of this invention is enhanced by the ability to obtain these mixed ester products by a one-step reaction employing polyoxyethylene glycols having molecular weights less than 1000. Ester products having the above-mentioned desirable properties are not possible when high molecular weight polyoxyethylene glycols are substituted in the one-step reaction procedure of this invention.

The ester products of the present invention are obtained by the single-step reaction of a triglyceride, a polyoxyethylene glycol having an average molecular weight less than 1000, and a mono- or dicarboxylic acid containing from 2 to 12 carbon atoms. Especially useful in the present invention are triglycerides derived from predominantly ethylenically unsaturated $C_{18}$ fatty acids, polyoxyethylene glycols having average molecular weights between 400 and 800, and aliphatic acids containing 2 to 12 carbon atoms or cycloaliphatic and aromatic acids containing from 7 to 12 carbon atoms. The ester compositions will contain from about 5 to 35% by weight triglyceride, 4 to 20 wt. % carboxylic acid and about 60 to 85 wt. % polyoxyethylene glycol. The ester products will generally have acid values of about 10 or below. About 0.1 to about 25% by weight of the ester is preferably dissolved in water to provide the useful aqueous lubricant solutions.

DETAILED DESCRIPTION

The mixed ester compositions of this invention are the reaction products of a triglyceride, a polyoxyethylene glycol of molecular weight less than 1000 and a short-chain monobasic or dibasic acid. The transesterification reaction is completed in a single step to obtain the mixed esters which are soluble in cold water in all proportions to provide clear aqueous lubricant solutions which do not separate on standing. The present lubricant esters have excellent lubricating properties.

To obtain the ester compositions of this invention any of the commonly known triglycerides can be employed and yied water soluble mixed ester products. Natural and synthetic fatty acid triglycerides including the drying, semi-drying and non-drying vegetable oils, animal oils and fats are useful and are within the scope of the present invention. Triglycerides of the above types include olive oil, palm oil, almond oil, ground nut oil, apricot kernel oil, linseed oil, castor oil, soybean oil, oiticica oil tung oil, crambe oil, coconut oil, peanut oil, rapeseed oil, neatsfoot oil, cottonseed oil, tallow, lard, whale oil and the like. The oils may be used as such or may be hydrogenated or modified prior to use. They may be used individually or a mixture of two or more triglycerides employed. For example, if a highly conjugated trilyceride such as tung oil or oiticica oil is used it may be advantageous to include a second oil of an unconjugated nature. Expecially useful trilycerides for the preparation of the instant ester compositions are those derived from predominantly ethylenically unsaturated $C_{18}$ fatty acids such as oleic acid, linoleic acid, linolenic acid and mixtures thereof. Oleic-linoleic acid oils and linolenic acid oils, and more particularly linseed oil and soybean oil, are especially useful triglycerides for use in the present invention.

The polyoxythylene glycols useful for the purpose of this invention have average molecular weights less than 1000 but preferably above about 200. It is possible to employ polyoxyethylene glycols containing higher and lower molecular weight materials so long as the resulting mixtures fall within the approximate foregoing ranges. A broad molecular weight distribution of the polyoxyethylene glycols is generally not detrimental to the lubricant properties, however, appreciable amounts of glycols having molecular weights greater than 1000 should not be present if optimum results are to be obtained. Best results are obtained with polyoxyethylene glycols having average molecular weights between about 400 and 800.

To achieve the improved water soluble mixed ester compositions of this invention one or more carboxylic acids are included when the triglyceride and low molecular weight polyoxyethylene glycol are reacted. Useful acids can generally be defined as low molecular weight short-chain mono-and dicarboxylic acids and, more specifically, contain from 2 to 12 carbon atoms. Acids suitable for use in the process include aliphatic, cycloaliphatic and aromatic acids which contain one or two carboxyl groups. Tri-and tetracarboxylic acids may also be employed if desired as may other polyfunctional compounds such as trimellitic anhydride. Useful cycloaliphatic and aromatic acids contain from about 7 to 12 carbon atoms and include such acids as benzoic acid, phenylacetic acid, toluic cid, phthalic acids, p-tert butyl benzoic acid, cyclohexanecarboxylic acid, cyclohexanedicarboxylic acid and the like. Aliphatic acids can either be branched or straight-chain and can contain from about 2 to about 12 carbon atoms. Useful aliphatic acids include oxalic acid, malonic acid, succinic acid, glutaric acid, adipic acid, azelaic acid, suberic acid, dodecanedioic acid, acetic acid, butyric acid, valeric acid, caproic acid, caprylic acid, capric acid, lauric acid and the like. Especially useful acids for the purpose of this invention are aliphatic, preferably saturated and straight-chain, mono- and dicarboxylic acids containing from about 6 to 10 carbon atoms.

Numerous water soluble mixed ester products can be obtained depending on the ratio of reactants employed. For best results however, both from the standpoint of water solubility and lubricant properties, the triglyceride will constitute about 5 to 35% by weight of the total reactant charge with the carboxylic acid and polyoxyethylene glycol comprising about 1 to 20% by weight and about 60 to 85% by weight, respectively. Extremely effective lubricant esters which are readily soluble in cold water are obtained with about 10 to 30% by weight triglyceride, 5 to 15% by weight carboxylic acid and 65 to 75% by weight polyoxyethylene glycol. These ester products are particularly useful if derived frm linseed or soybean oil, a $C_{6-10}$ straight-chain saturated mono- or dicarboxyic acid and polyoxyethylene glycol having a molecular weight from about 400 to 800.

Numerous advantages are realized when the above-described reactants are combined in the prescribed amounts as a unit charge and reacted in a single step. Most importantly, ester products having good lubricant properties and complete solubility in cold water in all proportions are obtained. Additional advantage is realized, however, from the fact that the soproduced esters have negative heats of solution.

While the above two features by themselves are useful and truly unexpected, there are still other important aspects of this invention including the ability to use low molecular weight polyoxyethylene glycols, the ability to achieve water solubility with reduced polyoxyethylene glycol contents and the ability to achieve water solubility regardless of the particular triglyceride used, which are also useful and highly desirable features. Previously, only high molecular weight polyoxyethylene glycols could be used if water solubility was to be achieved but it is now possible with this invention to use low molecular weight polyoxyethylene glycols and achieve the same result. Somewhat related to the ability to employ low molecular weight polyoxyethylene glycols is the fact that with this invention it is also possible to obtain water solubility using reduced levels of polyoxyethylene glycol. Through the use of low molecular weight short-chain carboxylic acids it is possible to reduce the polyoxyethylene glycol content by as much as 20% and still obtain water soluble products. By so doing, the triglyceride content in the product is also increased, in some cases by as much as 10% and thus the resulting ester composition has much improved lubrication properties. Still another surprising and useful aspect of this invention is the fact that contrary to previously known processes which yielded water soluble esters with only a few of the more compatible triglycerides, such as castor oil, it is now possible to render a wide variety of commonly available triglycerides completely soluble in cold water.

While the present invention is primarily directed to water soluble mixed ester products it is also possible, by utilizing reactant ratios outside the previously specified range, to obtain ester compositions which are not completely water-soluble but which are, nevertheless, extremely useful for their lubricant properties. These esters are typically readily emulsifiable with water without the use of external emulsifying aids and the resulting emulsions find general application in the treatment of fibers to reduce static charge buildup and improve the lubricity of the fiber and they are also highly efficient lubricants for metal working. These emulsions have the added advantage of improved stability, i.e. resistance to phase separation over lubricant emulsions formed with external emulsifiers. The improved emulsion properties apparently result from the presence of the mono- or dicarboxylic acid since similar ester compositions prepared in the same manner from a triglyceride and polyoxyethylene glycol but without the short-chain carboxylic acid do not possess these same characteristics.

The reaction of the triglyceride, polyoxyethylene glycol and mono- or dicarboxylic acid to obtain the useful mixed ester products is conducted in a single step in accordance with known transesterification procedures. The reaction mixture is typically maintained at an elevated temperature until an acid value less than about 10, more preferably less than about 6, is attained. The temperature of reaction may range from about 100°C to about 300°C but more usually will fall between about 175°C and 275°C. Water formed during the reaction is removed to facilitate esterification. While the use of reduced pressure is not necessary in carrying out the reaction it is often advantageous, especially in the latter stages of the reaction if low acid values are desired, in order to drive the reaction to completion. Catalysts are not essential to the successful completion of the transesterification, however, they are usually desirable in order to speed the rate of reaction. The amount and type of catalyst can be widely varied. Known catalysts such as tetrabutyl titanate, zinc acetate, sodium carbonate, sodium acid sulfate, p-toluene sulfonic acid, methane sulfonic acid, sulfuric acid, phosphoric acid and the like may be employed. The amount of catalyst will generally range between about 0.01 to 1.0% by weight of the total reactant charge. Most often the catalyst charge will be from about 0.03 to 0.5% by weight based on the total reactants.

The reaction may be conducted in an inert diluent which is unaffected under the reaction conditions employed. Hydrocarbon diluents, such as for example xylene, are useful in this process. Preferred diluents should be capable of forming azeotropes with water to facilitate removal of water formed during the reaction. If diluents are not employed, which is the most commonly practiced method of conducting the reaction, the mixed ester reaction product can be directly utilized, i.e., as obtained from the reactor, without any additional treatment.

The mixed ester products of this invention consist primarily of monoglycerides, diglycerides, unreacted triglycerides, monoesters of polyoxyethylene glycol, diesters of polyoxyethylene glycol and the like. Polymeric materials may also be present in small amounts particularly if the low molecular weight short-chain carboxylic acid is a difunctional acid. The various constituents and the amount of each of these constituents present in the resulting product is governed by the reactants and reaction conditions. While the makeup may vary considerably depending on the reaction temperature and pressure, amount and type of catalyst, ratio of reactants and the like, this compositional variation is not detrimental to the lubricant properties as long as the reaction is conducted in accordance with the foregoing description and within the specified ranges of reactant ratios.

The mixed esters of the present invention vary in physical form from low viscosity liquids to semi-solid masses. While most of the mixed ester compositions are fluid oils, highly viscous and even semi-solid products result if triglycerides, such as tallow, derived predominantly from saturated fatty acids are used. The clear liquid ester products which flow readily at room temperature are readily soluble in cold water in all proportions and give clear aqueous lubricant solutions which do not separate upon standing. With the more viscous oils or the semi-solid products it may be necessary to first heat or melt the ester product prior to addition of the water in order to obtain clear aqueous solutions. These products are, however, readily soluble upon melting and do not separate from solution even upon cooling. The mixed ester products of this invention generally have flash and fire points greater than 500°F with 210°F viscosities from 10 to 20 centistokes and 100°F viscosities from 60 to 120 centistokes, more preferably the 210°F and 100°F viscosities of these products are between 12 and 16 centistokes and 70 and 90 centistokes, respectively.

The instant ester compositions are excellent lubricants for both ferrous and nonferrous metals and are useful for a wide variety of other lubricating applications. They may be used as such or, as they are more commonly employed, in aqueous solutions. Aqueous solutions are particularly useful in forging, rolling, diecasting and metalworking operations, particularly where the working of hot metals is involved, since these solutions are capable of providing a thin uniform lubricant film on the surface of hot metals and since they also provide a high degree of cooling. These lubricants may also be used in machining operations such as drilling, grinding, polishing, etc. to increase the tool life and improve the finish on the machined article. The fact that the aqueous lubricant solutions are clear and do not separate is also advantageous. The present esters and solutions thereof may be applied to the metal and/or metalworking elements or the metal by spraying, immersing or by similar means. To improve the efficiency of the operation and reduce the cost, the lubricants may be collected, refiltered, if necessary, and reused.

For certain applications it is advantageous that these esters have negative heats of solution since the lubricant esters separate from solution at higher temperatures and are thus deposited on the surface of the hot metals or where friction occurs. As a result of this "plating out" maximum lubricating efficiency is provided at the points where it is needed most. This feature is also useful in certain rolling operations where heated rolls are employed since in this way a continuous lubricant film will be present on the surface of the roll and friction can be minimized thereby permitting more rapid rolling while retaining good surface quality. Numerous ther advantages for lubricants having negative heats of solution are evident to those skilled in the art.

The esters of this invention may be formulated with other additives, stabilizers, corrosion inhibitors, and the like, and they may be blended with one or more other petroleum or synthetic lubricants if desired. When employed in aqueous systems the concentration of the ester composition will normally range from about 0.1 to about 25% by weight even though these esters mix with cold water in all proportions. Aqueous solutions of the present mixed ester products typically have cloud points above 95°F.

In addition to being useful as lubricants for metals, the esters of this invention also find utility in other areas. Aqueous lubricant solutions of these esters are useful as finishing agents for polymeric fibers such as polyolefins, polyesters, polyamides and polyacrylonitriles. Such finishing agents are required during the processing of the fibers into yarns and fabrics to increase the surface lubricity of the fibers, thereby reducing the fiber-fiber friction and friction between the fibers and guides, draw pins, etc. of the process equipment. These lubricants can be applied to the fibers by spraying, immersing or the like. By lubricating the fibers it is possible to decrease filament breakage, reduce static charge buildup in the fibers and facilitate the various process steps. The present ester compositions are especially suited for use in polyester and polyamide fiber-forming operations. The esters may also be used for hydraulic fluids, paint formulations, cosmetic formulations, oil well drilling muds and most other uses where synthetic ester lubricants are commonly employed.

The following examples illustrate the invention more fully, however, they are not intended as a limitation on the scope thereof. All parts and percentages in the invention are on a weight basis unless otherwise indicated.

EXAMPLE I

To a glass reactor equipped with a stirrer, thermometer, H-trap connected to a water cooled condenser and nitrogen inlet were charged 840 grams (2.86 equivalents) soybean oil, 2380 grams (11.9 equivalents) polyethylene glycol (PEG) having an average molecular weight of 400 and 280 grams (2.98 equivalents) azelaic acid (EMEROX 1144). The weight ratio of oil:PEG 400: acid was 24:68:8. This mixture was heated with agitation while pulling a vacuum to dry the system. Tetrabutyltitanate catalyst (0.03 weight percent based on the total reactant charge) was then charged to the reactor and the reaction mixture heated to about 250°C under a nitrogen atmosphere for about 11 hours while periodically taking samples to determine the acid value (AV) After 11 hours reaction the product (AV 0.19) was completely soluble in cold water to give sparkling clear solutions. Heating was terminated at this point. The mixed ester clear solutions. Heating was terminated at this point. The mixed ester product had hydroxyl value of 141.2 and viscosities at 100°F and 210°F (ASTM D 445-65) of 78.8 centistokes and 12.9 centistokes, respectively.

To demonstrate the versatility of the resulting ester and the ability of the product to function as a lubricant, an aqueous solution of the ester was applied as a finish to a polyester yarn. Such finishes are commonly used to improve lubrication at the fiber-metal interface thereby reducing the static charge accumulation on the fiber during processing. The mixed ester was applied at 0.5% o.w.f. on 150 denier polyester which was solvent stripped to remove any previous finish. Finishes were applied from aqueous solutions using an Atlab Finish Applicator. Before testing, the treated yarns were conditioned for 24 hours at 70°F and 65% relative humidity. Frictional properties of the yarn were then measured with a Rothschild F-Meter holding the tension constant at 100 grams using a yarn speed of 100 meters per minute and a yarn/metal contact angle of 180°. Static properties were determined by insulating one of the pulleys and connecting it to a voltmeter and measuring the static "buildup" on the pulley in 8 seconds. The ester composition described above was compared to sorbitan monolaurate, a commercially available product commonly employed for textile finishing, and shown to have a lower coefficient of friction and a significantly lower voltage buildup (300 volts for the mixed ester as compared to 550 for the sorbitan ester) indicating improved fiber lubricity when the mixed ester product is used as a finishing agent.

EXAMPLE II

Employing a procedure similar to that described in Example I the following materials are charged to a reactor:

| | GRAMS CHARGED | WEIGHT RATIO |
|---|---|---|
| Cochin Coconut Oil | 120 | 24 |
| Polyethylene Glycol 400 | 340 | 68 |
| Azelaic Acid | 40 | 8 |

About one-half of the tetrabutyltitanate catalyst was added at the beginning of the heating and the remainder charged after a portion of the water had been removed. Heating (250°C) was terminated when the acid value of the reaction product reached 5.3. The resulting mixed ester product containing about 68% bound polyoxyethylene glycol, had a viscosity of 70.6 centistokes at 100°F, and was immediately soluble in cold tap water with essentially no agitation.

The effectiveness of the mixed ester product of this Example as a metal-working lubricant was determined using a Falex machine. This machine provided a convenient and reliable method for determining the film strength or load-carrying properties of lubricants under extreme pressures. The Falex wear test (ASTM D 2670-67) is conducted with a 60 gram sample of the ester product or, if aqueous solutions of the mixed ester lubricants are being evaluated, a 600 gram sample of the aqueous solution is used. The cup containing the lubricant is positioned so that the steel pin and blocks are completely immersed in the sample. The machine is started and an initial load of 300 pounds applied for 5 minutes. The load is then increased to 1000 pounds and maintained for 30 minutes. The difference between the readings taken at the beginning and the end of the 30 minute periods indicates the amount of wear. The mixed ester product of Example II showed only 47 units wear. This is a marked improvement over mineral oil of comparable viscosity which fails before the 1000 pound load level is reached and dioctyl sebacate which fails at the 300 pound load level after only 30 seconds operation. A 5% aqueous solution of the mixed ester evaluated on the Falex machine also registered only 71 units wear. These results demonstrate the superior lubricating propertis of the mixed ester products of the present invention.

EXAMPLE III

A reaction was conducted employing identical amounts and types of reactants as described in Example I. Zinc acetate (0.1 percent by weight based on the soybean oil) was used to catalyze the reaction. After about 5-½ hours of heating at 250°C the acid value dropped to 0.9. The resulting lubricant ester product had a hydroxyl value of 85.6, flash and fire point (ASTM D 92-66) of 550°F and 590°F, respectively, and a 210°F viscosity of 12.6 centistokes. The product was readily soluble in cold water producing a clear solution effective as a lubricant for both metal and fiber uses. When the above Example was repeated using polyoxyethylene glycol having an average molecular weight of about 800 a similar product was obtained.

EXAMPLES IV – VII

To demonstrate the versatility of this invention and the ability to obtain water soluble ester lubricants with triglycerides other than soybean oil and coconut oil, a series of runs were conducted in which PEG 400 and azelaic acid were reacted with linseed oil, palm oil, tallow and castor oil. In each of these runs the triglyceride constituted 24% of the charge with polyoxyethylene glycol (68%) and azelaic acid (8%) making up the remainder. The reactions were all conducted similarly, following the procedure of Example I. Physical properties and Falex test results for the resulting ester products are set forth below. Cloud points for the esters were obtained by determining the temperature at which printed matter was no longer legible through 100 mls of a 5% aqueous solution of the ester in a 250 ml glass beaker. At room temperature and below all of these products provide sparkling clear solutions, however, as these solutions are heated they become cloudy.

| RUN NO. | IV | V | VI | VII |
|---|---|---|---|---|
| Triglyceride | Linseed Oil | Palm Oil | Tallow | Castor Oil |
| Acid Value | 0.3 | 0.7 | 0.2 | 1.2 |
| 100°F Viscosity (cS) | 74.8 | 81.5 | 82.0 | 110 |
| 210°F Viscosity (cS) | 12.5 | 12.8 | 12.7 | 15.6 |
| Flash Point (°F) | 555 | 515 | 505 | 530 |
| Fire Point (°F) | 590 | 565 | 560 | 575 |
| Cloud Point (°F) | 97 | 102 | 100 | 100 |
| Units of Wear on the Falex Machine: | | | | |
| 100% Ester | 25 | 34 | 37 | 22 |
| 5% Ester in Water | 96 | 100 | 107 | 73 |

The ability to obtain clear solutions with palm oil and tallow is truly surprising in view of the fact that these saturated triglycerides are generally very difficult to even emulsify.

EXAMPLES VIII – XII

A series of water soluble soybean oils were prepared in accordance with the already described procedures. The polyoxyethylene glycol used had an average molecular weight of about 400 but the modifying acids were varied to include aliphatic and aromatic mono- and dicarboxylic acids. The weight ratio of soybean Oil:PEG 400: acid was 24:68:8. The following table lists the various acids used and the properties of the resulting esters.

| EXAMPLE NO. | ACID COMPONENT | ACID VALUE | CLOUD POINT (°F) |
|---|---|---|---|
| VIII | pelargonic | 1.4 | 102 |
| IX | p-tert-butylbenzoic | 0.5 | 91 |
| X | dodecanedioc | 1.5 | 118 |
| XI | isophthalic | 0.5 | 90 |
| XII | terephthalic | 2.0 | 88 |

All these esters provided sparkling clear solutions in concentrations of 5 to 25% using room temperature tap water. These esters had good lubricating ability both as the neat oils and in aqueous solution.

EXAMPLE XIII

A preparation was made using soybean oil, azelaic acid and polyoxyethylene glycol having an average molecular weight of 2000. The procedure, weight ratios of reactants and catalyst were the same as in Example II. The reaction was continued until an acid value less than 10 was achieved. The resulting ester product did not form a clear solution with room temperature water but was readily emulsifiable to provide a moderately stable emulsion.

EXAMPLE XIV

Soybean oil was modified following the procedure of Example I except that the reactant charge was varied. In this preparation the weight ratio of soybean oil:PEG 400: azelaic acid was 28:78:1. The ester product was readily soluble in water at room temperature and had good lubricating properties.

EXAMPLES XV – XVII

Palm oil, castor oil and coconut oil were charged as follows with PEG 400 and azelaic acid:

| | WEIGHT PERCENT OF TOTAL CHARGE | | | | |
|---|---|---|---|---|---|
| EXAMPLE | Palm Oil | Castor Oil | Coco Oil | PEG 400 | Azelaic Acid |
| XV | 30 | — | — | 60 | 10 |
| XVI | — | 30 | — | 60 | 10 |
| XVII | — | — | 26 | 65 | 9 |

These materials were reacted in the usual manner to obtain mixed ester products having acid values of 0.1, 2.6, and 2.8 respectively. The ester products demonstrated good lubricant properties when evaluated with the Falex machine and they formed clear aqueous solutions at room temperature.

EXAMPLE XVIII

The versatility of the present process and the ability to obtain useful ester products using low molecular weight short-chain carboxylic acids, even though the reactant ratios are outside the defined ranges, is evident from the following preparation where soybean oil, PEG 400 and azelaic acid were reacted at a weight ratio of 90:6:4. Tetrabutyltitanate was used to catalyze the reaction which was carried out at 220°C. The ester obtained (AV 5.4) did not form a clear solution with water but was readily emulsifiable in water without the use of external emulsifying aids. The ester had viscosities at 100°F and 210°F of 44cS and 9.2cS, respectively, with a 550°F flash point and 625°F fire point. A 5% aqueous emulsion of the ester showed essentially no wear at the end of the standard testing period in the Falex machine while the neat oil gave only 49 units wear.

We claim:

1. An aqueous lubricating composition comprising an aqueous solution of a water soluble mixed ester product obtained by the single-step transesterification of:
   a. a triglyceride selected from the group consisting of animal oils, animal fats, drying vegetable oils, semi-drying vegetable oils and non-drying vegetable oils;
   b. a polyoxyethylene glycol having an average molecular weight of from about 400 to 800; and c. a hydrocarbyl carboxylic acid containing one or two carboxyl groups and from 2 to 12 carbon atoms; said reactants (a), (b) and (c) respectively comprising 5 to 35%, 60 to 85% and 1 to 20 by weight of the total charge, said solution being clear at room temperature but having a distinct cloud point above 95°F.

2. The aqueous solution of claim 1 wherein the mixed ester product is derived from (a) an oleic- linoleic acid oil or linoleic acid oil, (b) a polyoxyethylene glycol having an average molecular weight from 400 to 800 and (c) a saturated, straight-chain aliphatic mono- or dicarboxyic acid containing about 6 to 10 carbon atoms.

3. The aqueous solution of claim 2 wherein the mixed ester product has an acid value less than about 10.

4. The aqueous solution of claim 2 containing from about 0.1% to 25% by weight of a mixed ester derived from linseed oil or soybean oil.

* * * * *